(12) United States Patent
Shan et al.

(10) Patent No.: US 6,906,208 B2
(45) Date of Patent: Jun. 14, 2005

(54) MESOPOROUS MATERIAL AND USE THEREOF FOR THE SELECTIVE OXIDATION OF ORGANIC COMPOUNDS

(75) Inventors: Zhiping Shan, Delft (NL); Thomas Maschmeyer, Delft (NL); Jacobus Cornelius Jansen, Delft (NL)

(73) Assignee: ABB Lummus Global Inc., Bloomfield, NJ (US)

( * ) Notice: Subject to any disclaimer, the term of this patent is extended or adjusted under 35 U.S.C. 154(b) by 0 days.

(21) Appl. No.: 10/246,495

(22) Filed: Sep. 18, 2002

(65) Prior Publication Data

US 2003/0017943 A1 Jan. 23, 2003

Related U.S. Application Data

(63) Continuation-in-part of application No. 09/995,227, filed on Nov. 27, 2001, now Pat. No. 6,762,143, which is a continuation-in-part of application No. 09/390,276, filed on Sep. 7, 1999, now Pat. No. 6,358,486.

(51) Int. Cl.[7] .................... C07D 301/10; C07D 301/12; C07D 301/14
(52) U.S. Cl. .................. 549/533; 549/525; 549/529; 549/531; 549/532; 549/534; 549/536; 549/537
(58) Field of Search ................ 549/533, 525, 549/529, 531, 532, 534, 536, 537; 546/537

(56) References Cited

U.S. PATENT DOCUMENTS

| | | | |
|---|---|---|---|
| 3,959,174 A | 5/1976 | Winyall et al. | 423/338 |
| 5,057,296 A | 10/1991 | Beck | 423/277 |
| 5,098,684 A | 3/1992 | Kresge et al. | 423/277 |
| 5,102,643 A | 4/1992 | Kresge et al. | 423/328 |
| 5,108,725 A | 4/1992 | Beck et al. | 423/263 |
| 5,110,572 A | 5/1992 | Calabro et al. | 423/328 |
| 5,191,134 A | 3/1993 | Le | 585/446 |
| 5,191,148 A | 3/1993 | Degnan et al. | 585/724 |
| 5,264,203 A | 11/1993 | Beck et al. | 423/703 |
| 5,374,747 A | 12/1994 | Saxton | 549/531 |
| 5,539,710 A | 7/1996 | Tokushuku et al. | 369/32 |
| 5,622,684 A | 4/1997 | Pinnavaia et al. | 423/702 |
| 5,672,556 A | 9/1997 | Pinnavaia et al. | 502/63 |
| 5,707,917 A | 1/1998 | Geus et al. | 502/209 |
| 5,795,555 A | 8/1998 | Alive et al. | 423/326 |
| 5,811,599 A | 9/1998 | Alive et al. | 568/771 |
| 5,849,258 A | 12/1998 | Lujano et al. | 423/700 |
| 5,853,566 A * | 12/1998 | Kraushaar-Czarnetzki et al. | 208/109 |
| 5,948,683 A | 9/1999 | Koermer et al. | 436/37 |
| 5,951,962 A | 9/1999 | Müller et al. | 423/702 |
| 6,133,186 A | 10/2000 | Gosselink et al. | 502/67 |
| 6,309,998 B1 | 10/2001 | Bowman et al. | 502/242 |
| 2003/0017943 A1 | 1/2003 | Shan et al. | 502/243 |

FOREIGN PATENT DOCUMENTS

| | | |
|---|---|---|
| EP | 0 814 058 A1 | 4/1997 |
| EP | 0 985 636 A1 | 9/1999 |
| EP | 1 134 189 A1 | 3/2000 |
| WO | WO 00/15551 | 3/2000 |
| WO | WO 01/72635 A1 | 10/2001 |
| WO | WO 02/40402 A1 | 5/2002 |

OTHER PUBLICATIONS

Notification of Transmittal of the International Search Report or the Declaration and International Search Report for PCT/US03/30009, dated Sep. 17, 2003.

Cabera, et al., "Surfactant Assisted Synthesis of Mesoporous Alumina Showing Continuously Adjustable Pore Sizes", advanced materials, (1999) 33 No. 5 pp. 279–381.

* cited by examiner

*Primary Examiner*—Ba K. Trinh
(74) *Attorney, Agent, or Firm*—Dilworth & Barrese, LLP

(57) ABSTRACT

A material especially useful for the selective oxidation of hydrocarbons and other organic compounds includes a non-crystalline, porous inorganic oxide having at least 97 volume percent mesopores based on micropores and mesopores, and at least one catalytically active metal selected from the group consisting of one or more transition metal and one or more noble metal.

5 Claims, 5 Drawing Sheets

MESOPOROUS MATERIAL AND USE THEREOF FOR THE SELECTIVE OXIDATION OF ORGANIC COMPOUNDS

CROSS-REFERENCE TO RELATED APPLICATIONS

The present application is a continuation in part of U.S. application Ser. No. 09/995,227 filed Nov. 27, 2001 now U.S. Pat. No. 6,762,143 and incorporated by reference herein, which is a continuation in part of U.S. application Ser. No. 09/390,276 filed Sep. 7, 1999, now issued as U.S. Pat. No. 6,358,486 B1, to which priority is claimed.

BACKGROUND

1. Field of the Invention

The present invention relates to a mesoporous material, particularly a catalytic material, and use of the mesoporous material for the selective oxidation of organic compounds, particularly hydrocarbons.

2. Background of the Prior Art

Various processes and catalysts are known for the selective oxidation of organic compounds. For example, U.S. Pat. No. 5,948,683 (Koermer et al.) discloses a catalytic material for the selective oxidation of unsaturated hydrocarbons in the presence of carbon monoxide. The catalytic material includes a phosphated ceria made by mixing ceria particles with a solution of phosphates, and then calcining the particles after separation from the solution.

U.S. Pat. No. 5,811,599 (Alive et al.) discloses a process for the oxidation of hydrocarbons using an aqueous solution of hydrogen peroxide in the presence of a titanium silicate catalyst.

U.S. Pat. No. 5,707,917 (Geus et al.) discloses a catalyst for the selective oxidation of hydrocarbons which comprises a support based on one or more metal oxides and vanadium-phosphorus oxide dispersed over the surface of the support. The process comprises an oxidation and reduction phase. The hydrocarbon is contacted with the catalyst in the reduction phase and in oxidized or non-oxidized form is adsorbed onto the catalyst. The loaded catalyst is then brought into the oxidation phase wherein the desired product is formed in the presence of gaseous oxygen and subsequently separated.

There is yet need for an improved process and catalyst for the selective oxidation of hydrocarbons and other organic compounds.

SUMMARY OF THE INVENTION

A material is provided herein which comprises a non-crystalline, porous inorganic oxide having at least 97 volume percent mesopores based on micropores and mesopores, and at least one catalytically active metal selected from the group consisting of one or more transition metal and one or more noble metal. Also provided herein are a method for making the material and use of the material as a catalyst for the selective oxidation of organic compounds.

The process and catalyst herein provide for the selective oxidation of hydrocarbons and other organic compounds with very high selectivity.

BRIEF DESCRIPTION OF THE DRAWINGS

Various embodiments are described below with reference to the drawings wherein.

DETAILED DESCRIPTION OF PREFERRED EMBODIMENT(S)

Figure 1A:
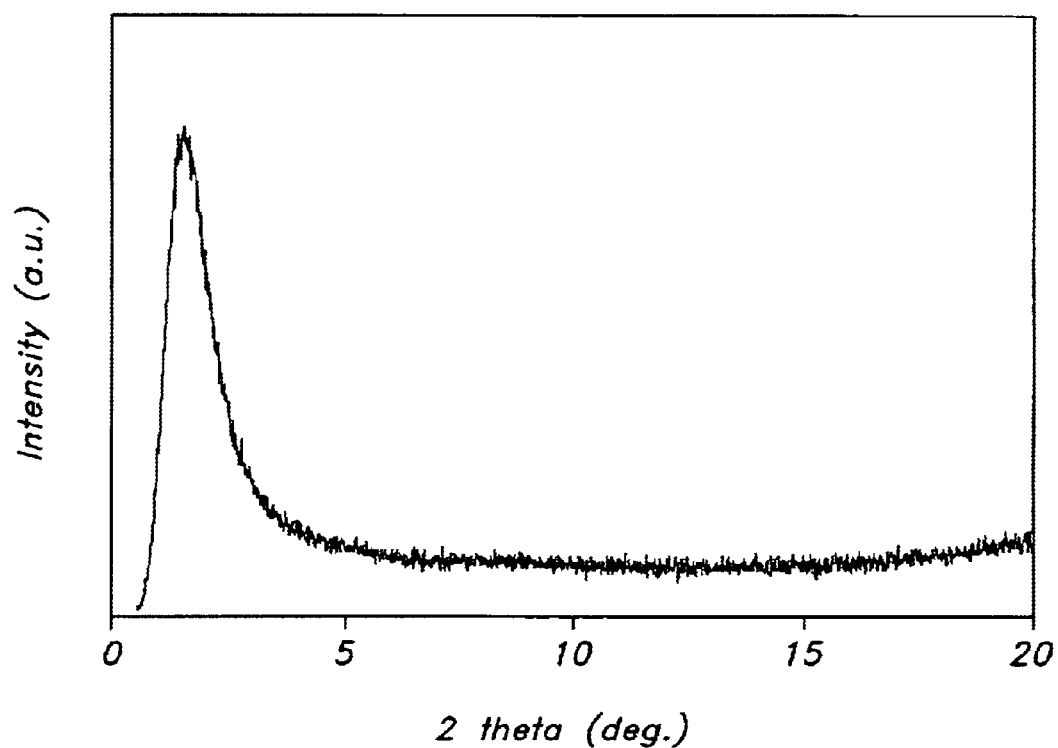
FIG. 1A is a plot showing the X-ray diffraction pattern of the catalyst material of Example 1.

The catalyst of the present invention includes a three-dimensional, stable, porous inorganic oxide material that is substantially mesoporous in structure. The material possesses a non-crystalline, but regularized (pseudo-crystalline) structure. Mesoporous materials are described in U.S. Pat. No. 6,358,486 B1, which is herein incorporated by reference in its entirety. The catalyst further includes one or more noble metal and/or one or more transition metal.

The amorphous inorganic oxide material of the present invention generally contains both mesopores and micropores. Micropores are defined as pores having a diameter of less than about 2 nm. Mesopores are defined as pores having a diameter of from about 2 nm to about 50 nm. The inorganic oxide material of the present invention has a volume percentage of mesopores of at least about 97% and preferably at least about 98%.

A method for making a preferred porous silica-containing catalyst support is described in U.S. Pat. No. 6,358,486 B1. The average mesopore size of the preferred catalyst as determined from $N_2$-porosimetry ranges from about 2 nm to about 25 nm. Generally, the mesoporous inorganic oxide is prepared by heating a mixture of (1) a precursor of the inorganic oxide in water, and (2) an organic templating agent that mixes well with the oxide precursor or the oxide species generated from the precursor, and preferably forms hydrogen bonds with it.

The starting material is generally an amorphous material and may be comprised of one or more inorganic oxides such as silicon oxide or aluminum oxide, with or without additional metal oxides. The silicon or aluminum atoms may be replaced in part by catalytically active transition metal atoms such as titanium, vanadium, copper, zirconium, manganese, zinc, chromium, molybdenum, tungsten, nickel, cobalt and iron and the like. The composition by weight of the transition metal is preferably up to about 60%, more preferably from about 0.001% to about 20% based on the total weight of the catalyst. The additional metals may optionally be incorporated into the material prior to initiating the process for producing a structure that contains mesopores. For example, homogeneous synthesis mixtures containing transition metal alkoxide, silicon or aluminum alkoxide (e.g., tetraethyl orthosilicate "TEOS", or aluminum isopropoxide), and organic templating agent can be prepared. The synthesis mixture can then be aged, dried, and calcined to produce a mesoporous structure. Drying of the synthesis mixture can be performed by heating the synthesis mixture to a drying temperature of from about 50° C. to about 150° C., preferably 60° C. to about 120° C., for a period of time sufficient to drive off the water and/or volatile organic liquids. Calcining of the dried mixture can be performed by heating the dried mixture to a calcining temperature of from about 300° C. to about 1,000° C., preferably from about 400° C. to about 700° C., for a period of time sufficient to form the mesoporous structure. Calcining times typically range from about 2 hours to about 40 hours, depending, at least in part, on the calcining temperature.

After heating to remove water and/or volatile organic compounds and before calcining, there is an optional step of heating the dried mixture in a container at a temperature of from about 130° C. to about 200° C. for a period of time of from about 2 hours to about 96 hours. This step can be used to manipulate the mesopore size, surface area and pore volume of the final composition.

Also, after preparation of the material, cations in the system may optionally be replaced with other ions such as those of an alkali metal (e.g., sodium, potassium, lithium, etc.).

The organic mesopore-forming templating agent is preferably a glycol (a compound that includes two or more hydroxyl groups), such as glycerol, diethylene glycol, triethylene glycol, tetraethylene glycol, propylene glycol, and the like, or member(s) of the group consisting of triethanolamine, sulfolane, tetraethylene pentamine and diethylglycol dibenzoate. Preferably, the templating agent has a boiling point of at least about 150° C.

The mesoporous catalyst support is a pseudo-crystalline material (i.e. —no crystallinity is observed by presently available x-ray diffraction techniques). The wall thickness of the mesopores is preferably from about 3 nm to about 25 nm. The surface area of the catalyst support as determined by BET ($N_2$) preferably ranges from about 400 m$^2$/g to about 1200 m$^2$/g. The catalyst pore volume preferably ranges from about 0.3 cm$^3$/g to about 2.2 cm$^3$/g.

During mixing, the appropriately selected active metal forms complexes with the templates (e.g., triethanolamine, or "TEA"). After drying the complexes together with free organic compound (such as TEA) act as a templating agent for the mesopores. Next, during calcining, the complexes decompose; and any organic species are removed. Consequently, transition metals homogeneously coat the internal surfaces of the mesopores. Depending on the loading of the transition metals, the coordination states of these transition metals can be controlled. Most of the active sites are easily accessible because they are preferentially enriched on the mesopore surfaces. In addition, the three-dimensional mesopore system also facilitates intraparticle mass transfer.

The inorganic oxide support, with or without transition metal, can be further modified by incorporation therein of a catalytically effective amount of one or more noble metals such as gold (Au), silver (Ag), platinum (Pt), palladium (Pd), iridium (Ir), rhodium (Rh), ruthenium (Ru), rhenium (Re) or osmium (Os). These noble metals can form nanosized particles having a diameter of 10 nm or less in the mesopores. The percentage by weight of the noble metal can range up to about 60%, preferably from about 0.1% to about 40%, based on the total catalyst weight.

The noble metal can be incorporated into the inorganic mesoporous oxide by any suitable method such as ion exchange or by impregnating the inorganic oxide with a solution of a soluble, decomposable compound of the noble metal, then washing, drying, and subjecting the impregnated inorganic oxide to a process such as calcining to decompose the noble metal compound, thereby producing an activated catalyst having free noble metal in the pores of the inorganic oxide. Suitable noble metal compounds include salts such as nitrates, chlorides, ammonium complexes, and the like.

Washing of the noble metal impregnated inorganic oxide catalyst is optionally performed with water to remove some anions. Drying of the catalyst to remove water and/or other volatile compounds can be accomplished by heating the catalyst to a drying temperature of from about 50° C. to about 190° C. Calcining to activate the catalyst can be performed at a temperature of from about 150° C. to about 600° C. for a sufficient period of time. Generally, calcining can be performed for 2 to 40 hours depending, at least in part, on the calcining temperature.

The resulting catalyst can be employed in selective oxidation processes such as described below:

A) Epoxidation of alkenes to produce epoxides. Suitable alkenes include $C_2$ to $C_{20}$ unsaturated hydrocarbon compounds such as, for example, ethylene, propylene, the butenes (1-butene, 2-butene, isobutylene) butadiene, the pentenes, linear or branched chain hexene, 1-octene, cyclohexene, and the like. Oxidizing agents can include oxygen, oxygen-containing gas, hydrogen peroxide ($H_2O_2$), nitrogen oxides, organic hydroperoxides, organic peracids, and the like. Epoxidation is typically carried out at a temperature of from about 30° to about 300° C., preferably 50° C. to about 250° C., a pressure of from about atmospheric to about 40 bars, and a space velocity of from about 10 WHSV to about 2000 WHSV. The reaction can be carried out in the gas phase, liquid phase, or mixed (gas/liquid) phase.

B) Partial oxidation of alkanes to produce ketonic or alcoholic derivatives. Suitable alkanes include propane, butane, pentane, cyclohexane, and the like. Suitable oxidizing agents can include oxygen, oxygen-containing gas, hydrogen peroxide, nitrogen oxides, organic hydroperoxides, and organic per-acids. Partial oxidation of alkanes to ketones is typically carried out at a temperature of from about 0° C. to about 200° C., a pressure of from about 1 bar to about 30 bars, and a space WHSV velocity of from about 100 hr$^{-1}$ to about 100,000 hr$^{-1}$. Alcohol production normally is carried out at a temperature of from about 60° C. to about 450° under a pressure of up to about 60 bars. The reaction can be carried out in the gas phase, liquid phase, or mixed phases.

C) Partial oxidation of alcohols. Suitable alcohols include, for example, benzyl alcohol, phenylethanol, phenol, and cinnamyl alcohol. Suitable oxidizing agents can include oxygen, oxygen-containing gas, hydrogen peroxide, nitrogen oxides, organic hydroperoxides, and organic per-acids. For example, benzaldehyde can be obtained by partial oxidation of benzyl alcohol using a catalyst of the present disclosure containing, e.g., copper (Cu), at about 300° C. to about 500° C. and under a pressure up to about 20 bars.

D) Hydroxylation of aromatic compounds to add hydroxyl group(s) to the aromatic ring structure. Said aromatic compounds preferably include benzene and toluene, although other aromatic compounds can also be used. Suitable oxidizing agents can include oxygen, oxygen containing gas, hydrogen peroxide, nitrogen oxides, organic hydroperoxides, and organic per-acids. Benzene oxidized into phenol and toluene into cresols can be conducted at a temperature from 25° C. to 500° C. and up to a pressure of 65 bars. The process also can be carried out in a distillation column reactor at a temperature in the range of from above 100° C. to 270° C. and a benzene partial pressure in the range of from about 0.1 atm to about 45 atm.

E) Ammoximation of ketones with ammonia ($NH_3$) and hydrogen peroxide or nitrogen oxide to produce corresponding oximes. Suitable ketones include, for example, acetone, methylethyl ketone (MEK), acetophenone, cyclohexanone, cyclododecanone, and the like. Reaction conditions typically include a temperature of from about 25° C. to about 150° C., preferably 40° C. to about 120° C., and a pressure of from about 1 to 10 atmospheres, preferably 1 to 5 atmospheres.

Various features of the invention are illustrated by the Examples given below. X-ray powder diffraction patterns (XRD) of the resulting materials were recorded using $CuK_\alpha$ radiation on a Philips PW 1840 diffractometer equipped with a graphite monochromator. The samples were scanned in the range of 0.5–40° 2θ with steps of 0.02°. Transmission electron microscopy (TEM) was performed using a Philips CM30T electron microscope with a LaB6 filament as the source of electrons operated at 300 kV. Nitrogen sorption isotherms were measured on the Quantachrome Autosorb-6B at 77 K. Mesoporosity was calculated using the BHJ model. All composition parts are by weight unless indicated otherwise.

EXAMPLE 1

A catalyst of the present invention containing titanium was prepared and tested in accordance with the following procedure. First, 1.1 parts of titanium (IV) n-butoxide was mixed with 35.0 parts of tetraethyl orthosilicate ("TEOS"). Then 25.3 parts of triethanolamine ("TEA") were added drop-wise into the above mixture while stirring. After stirring for 1 hour, 21.3 parts of deionized water was drop-wise added into the above mixture while stirring. After another 1 hour of stirring, 17.3 parts of tetraethylammonium hydroxide ("TEAOH") (25%) was added drop-wise into the above-mixture. The final homogeneous mixture was aged at room temperature for 24 hours, dried at 100° C. for 24 hours and then calcined at 700° C. for 10 hours in a ramp rate of 1° C. $min^{-1}$ in air.

Figure 1B:
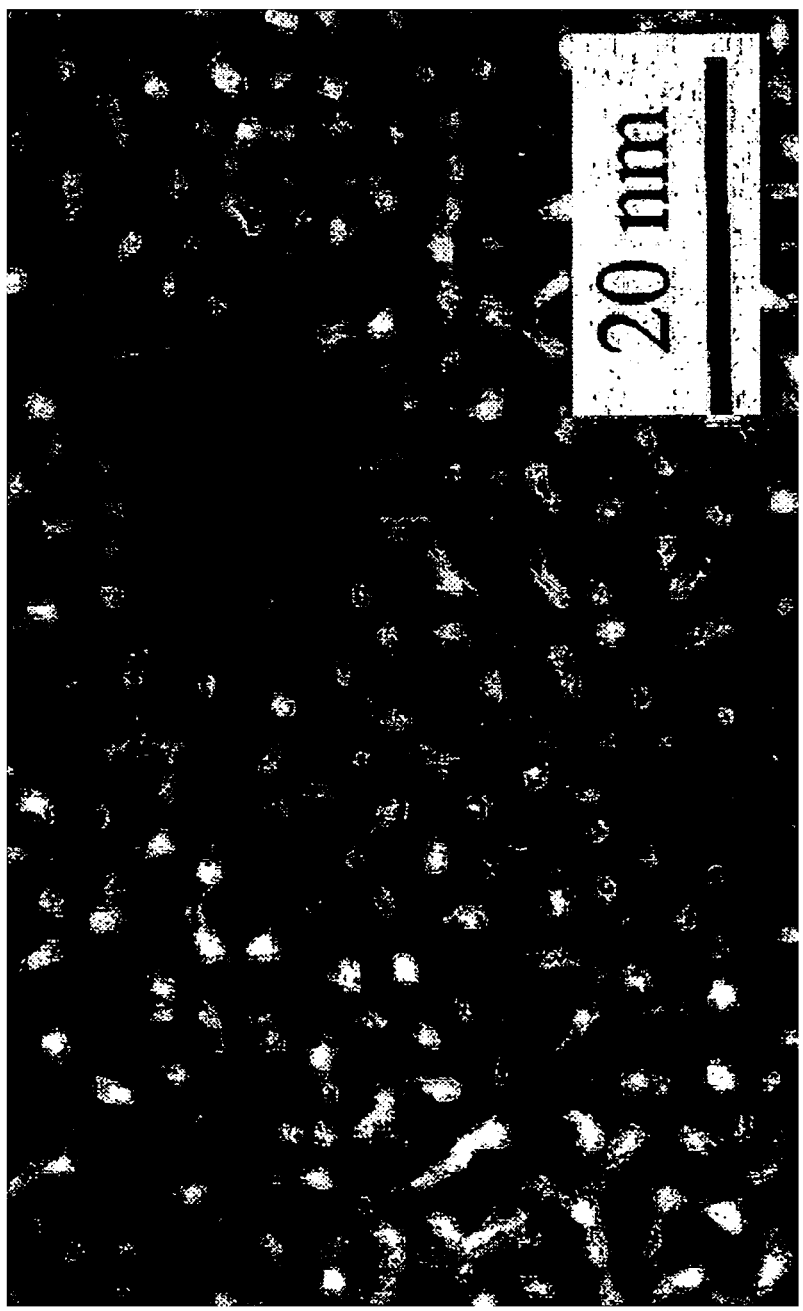
FIG. 1B is a transmission electron microscopy image of the catalytic material of Example 1.
Figure 2:
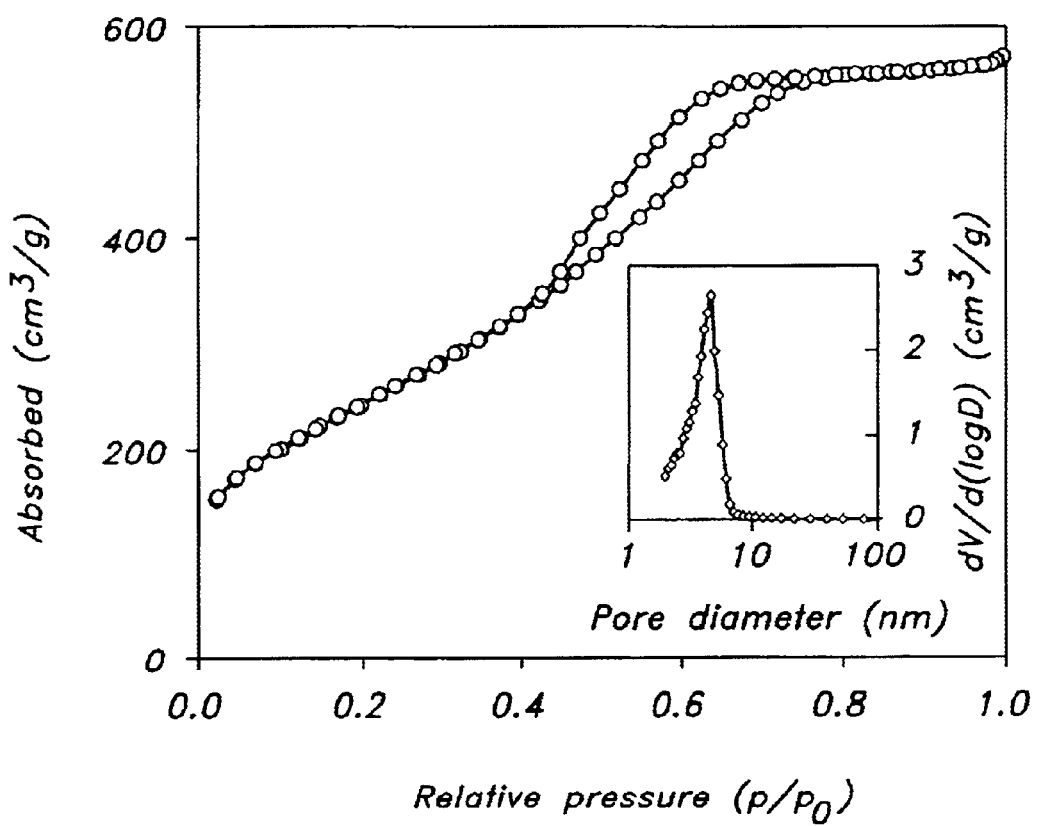
FIG. 2 graphically presents pore volume and pore size data pertaining to the catalytic material of Example 1.

The XRD pattern of the resulting material is shown in FIG. 1A, and reveals only one intensive peak between 0.5° and 2.5° at about 1.0° in 2θ, indicating that the product was a meso-structured material. FIG. 1B is a TEM image of the resulting material. FIG. 1B shows that curved and tortuous pores are randomly connected to form a three-dimensional pore network. The BET surface area of the material as determined by nitrogen absorption was about 917 $m^2/g$. Referring to FIG. 2, the average mesopore diameter of the material was 4.5 nm and the total pore volume was about 0.89 $cm^3/g$.

Next cyclohexene epoxidation was used as model reaction to demonstrate and quantify catalytic activity using tert-butyl hydroperoxide as an oxidant and was carried out at 40° C. under $N_2$. The reaction mixture consisted of 1 part catalyst, 9.6 parts cyclohexene (99%, dried using anhydrous $MgSO_4$ before use) and 13.2 parts dichloromethane (99%) Samples were analyzed by gas chromatography (WAX 52 CB). After 6 hours, about 45.6% of the cyclohexene was converted with almost 100% selectivity. The turnover frequency (defined as moles cyclohexene converted per mole of titanium per hour) was 20.2 $h^{-1}$.

COMPARATIVE EXAMPLE A

A titanium bearing catalyst not in accordance with the present invention, designated as Ti-MCM-41 was synthesized according to a procedure set forth in a previous report (L. Y. Chen, G. K. Chuah, S. Jaenicke, Catal. Lett. 50 (1998) 107.) It had BET surface are of 934 $m^2/g$ and an average pore diameter of about 3.3 nm. It was tested under the identical conditions as example 1, but it showed the turnover frequency of only 3.6 $h^{-1}$, which was less than 20% of the cyclohexene conversion achieved by the catalyst of Example 1.

EXAMPLE 2

Nano-sized particles of gold were introduced into the catalyst prepared in Example 1. An aqueous solution of $AuCl_4^-$ was prepared by adding 0.34 parts by weight of $HAuCl_4.4H_2O$ into 400 parts of $H_2O$. This was heated to 70° C., and its pH was adjusted using aqueous NaOH solution to about 7.0. Then 2 parts of the catalyst of Example 1 were suspended in the above solution, the pH was adjusted again to 7.0. The suspension was aged at 70° C. for 1 hour, and washed 3 times with distilled water, dried at 100° C. for 2 hours, and finally calcined in air at 300° C. for 4 hours.

Vapor-phase epoxidation of propylene to propylene oxide was carried out in a vertical fixed-bed quartz reactor filled with catalyst. The reactant feed contained 10 vol. % each of $C_3H_6$, $H_2$ and $O_2$ in Ar at a gaseous hourly space velocity (GHSV) of 10,000 $h^{-1}$ ml $g^{-1}$ of catalyst. The reaction temperature was kept at 120° C. The feed and products were analyzed by on-line gas chromatography(GC). About 3.5% propylene was converted to propylene oxide with a selectivity of about 96%.

EXAMPLE 3

A siliceous material was synthesized according to the procedure of Example 1 of U.S. Pat. No. 6,358,486 as follows:

First, 1.3 parts by weight aluminum isopropoxide was dissolved in 39.1 parts tetrapropylammonium hydroxide (40%) aqueous solution. Next, 47.88 parts TEA (97%) and 14.0 parts water were mixed. The aqueous TEA mixture was added drop-wise (8–10 g/min) to the aluminum containing mixture under stirring. Finally, 33.1 parts TEOS (98%) was added drop-wise (4–6 g/min) to the resulting mixture while stirring. The final mixture was aged at room temperature for 48 hours spread out in a dish to form a layer that had a height of 1.0–1.2 cm and dried at 100° C. for 18 hours in a static air furnace. The resulting material was calcined in air using the following procedure: the material was heated to 500° C. with a heating rate of 1° C./min, then held for 4 hours, then heated to 550° C. with a heating rate of 1° C./min, then held for 10 hours.

The resulting material was used to prepare a silver containing catalyst by the impregnation into the material of $AgNO_3$ aqueous solution. After being impregnated, the material was calcined at 250° C. for 4 hours. The impregnated catalyst was analyzed using ICP and revealed about 30.5% of silver loading.

The silver-containing catalyst was kept in a microflow reactor under atmospheric condition at 220° C. The reactant stream contained 20 vol % ethylene, 40 vol % oxygen and 40 vol % nitrogen. The total reactant stream GHSV was 4,500 $hr^{-1}$. The products were analyzed by gas chromatography. Within an hour, the conversion of ethylene reached 19.8%, and the selectivity to ethylene oxide was about 29%.

EXAMPLE 4

Figure 3:
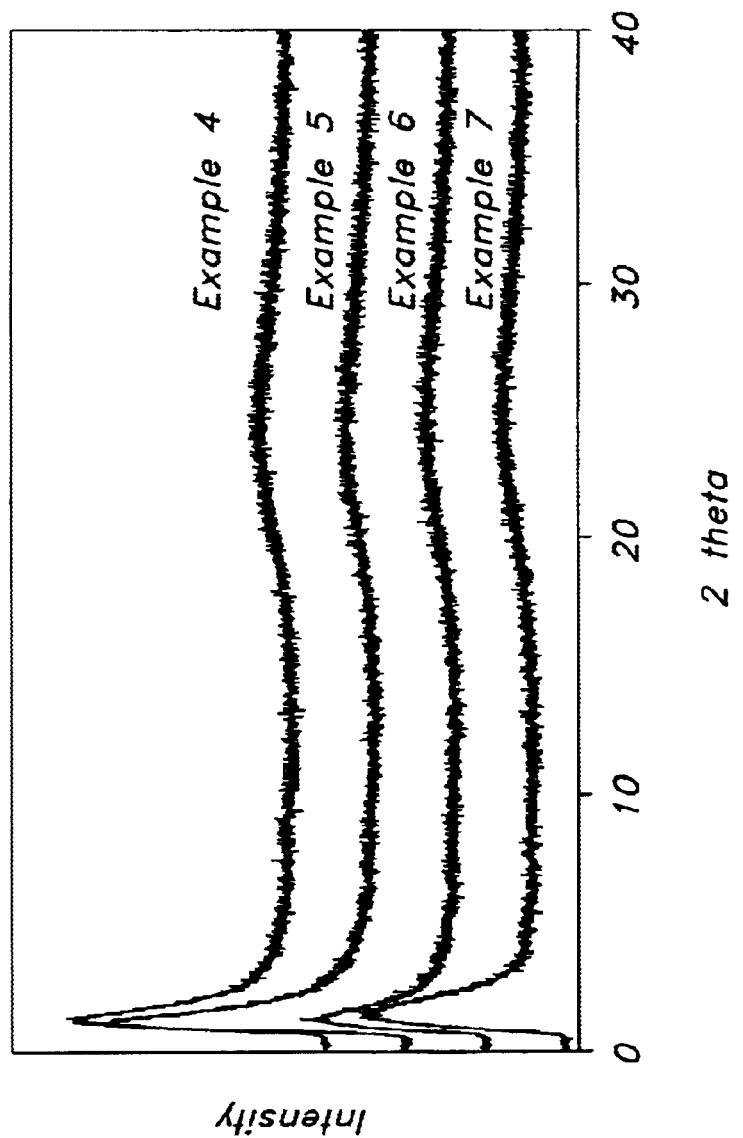
FIG. 3 is a graph showing the X-ray diffraction patterns of the catalyst materials of Examples 4, 5, 6 and 7; and, FIG. 4 is a graph showing the X-ray diffraction pattern of the catalyst material of Example 8.

1.7 Parts of titanium (IV) n-butoxide (99%) was mixed with 106 parts of TEOS (98%). Then a mixture of 77 parts TEA (97%) and 58 parts of deionized water were added drop-wise into the above mixture while stirring. After about 1 hour stirring, 63 parts of TEAOH (25%) was added drop-wise to the mixture. The Si/Ti molar ratio of the synthesis mixture was 100. The final homogeneous mixture was aged at room temperature for 24 hours, dried at 98° C. for 24 hours and then calcined at 650° C. for 10 hours at a ramp rate of 1° C./min in air. The XRD pattern of the material is shown in FIG. 3.

EXAMPLE 5

The same procedure as in Example 4 was followed except that 3.4 parts by weight of titanium (IV) n-butoxide were used and the Si/Ti ratio of the mixture was 50. The XRD pattern of the resulting material is shown in FIG. 3.

EXAMPLE 6

The same procedure as in Example 4 was followed except that 8.6 parts of titanium (IV) n-butoxide were used, and the Si/Ti ratio was 20. The XRD pattern of the resulting material is shown in FIG. 3.

EXAMPLE 7

The same procedure as in Example 4 was followed except that 17.2 parts of titanium (IV) n-butoxide were used and the Si/Ti ratio was 10. The XRD pattern of the resulting material is shown in FIG. 3.

As can be seen from Examples 4–7, adding the appropriate amounts of titanium compound in the initial synthesis mixture can easily control the titanium loading of the catalyst material of the present invention. The XRD patterns of the resulting materials of Examples 4–7 indicate that these materials are mesoporous.

EXAMPLE 8

First, 1.2 parts (by weight) of chromium (III) acetylacetonate (97%) was mixed with 34.5 parts of TEOS (98%). Then 25 parts of TEA (97%) was added drop-wise into the above mixture while stirring. After stirring for 1 hour, 18.8 parts of deionized water was drop-wise added into the above mixture while stirring. After another 1 hour of stirring, 20.5 parts of tetraethylammonium hydroxide (25%) was added drop-wise into the above mixture. The final homogeneous mixture was aged at room temperature for 24 hours, dried at 100° C. for 24 hours. The dried gel was heated in an autoclave at 180° C. for 8 hours, and finally calcined at 650° C. for 10 hours in a ramp rate of 1° C. $min^{-1}$ in air.

Figure 4:
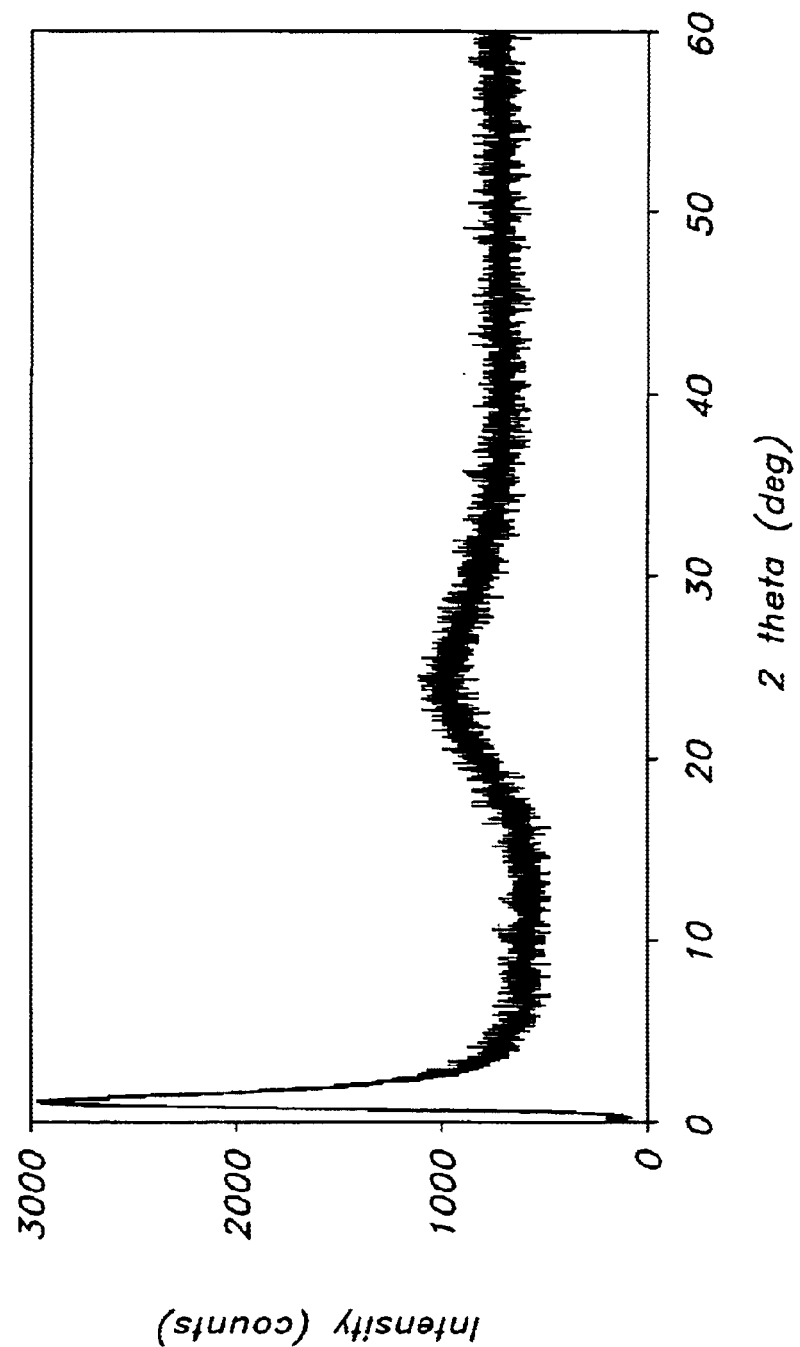

FIG. 4 shows the XRD pattern of this material, presenting an intensive peak at around 1.3° in 2θ. Nitrogen adsorption reveals the surface area of 618 $m^2$/g, the pore volume of 0.67 $cm^3$/g and the average pore size diameter of 5.5 nm. The data show that the chromium-containing material of this Example 8 is mesoporous in structure. This material was tested as a catalyst for cyclohexene epoxidation under identical conditions in Example 1. After six hours, about 46% of the cyclohexene was converted with a selectivity of about 94% to cyclohexene epoxide.

While the above description contains many specifics, these specifics should not be construed as limitations on the scope of the invention, but merely as exemplifications of preferred embodiments thereof. Those skilled in the art will envision many other possibilities within the scope and spirit of the invention as defined by the claims appended hereto.

What is claimed is:

1. A process for the selective oxidation of an alkene to a corresponding epoxide comprising:

contacting the alkene with an oxidizing agent under epoxidation reaction conditions in the presence of a catalyst which includes a non-crystalline, porous inorganic oxide containing silicon having at least 97 volume percent randomly interconnected mesopores based on micropores and mesopores, and at least one catalytically active metal selected from the group consisting of one or more transition metal and one or more noble metal.

2. The process of claim 1 wherein the alkene is selected from the group consisting of ethylene, propylene, 1-butene, 2-butene, isobutylene, butadiene, pentene, hexene, 1-octene and cyclohexene, the oxidizing agent is selected from the group consisting of oxygen, oxygen-containing gas, hydrogen peroxide, nitrogen oxide, organic hydroperoxide and organic peracid, and the epoxidation reaction conditions include a temperature of from about 50° C. to about 250° C., a pressure of from about atmospheric pressure to about 60 bars, and a space velocity of from about 10 WHSV to about 2000 WHSV.

3. The process of claim 1 wherein the catalytically active metal is selected from the group consisting of titanium, chromium, vanadium, gold and silver.

4. The process of claim 1 wherein the catalytically active transition metal is selected from the group consisting of titanium, vanadium and chromium.

5. The process of claim 1 wherein the catalytically active noble metal is gold or silver.

* * * * *